United States Patent

Varescon et al.

[11] Patent Number: 6,150,083
[45] Date of Patent: Nov. 21, 2000

[54] PHOTOGRAHIC SILVER HALIDE MATERIAL AND PROCESS FOR PREPARING SILVER IMAGES

[75] Inventors: Francois Varescon, Neu-Isenburg; Reinhold Rüger, Rödermark, both of Germany

[73] Assignee: Agfa-Gevaert, N.V., Mortsel, Belgium

[21] Appl. No.: 08/964,973

[22] Filed: Nov. 5, 1997

[51] Int. Cl.⁷ .................................... G03C 1/18
[52] U.S. Cl. ..................... 430/585; 430/264; 430/588
[58] Field of Search .................... 430/585, 588, 430/264

[56] References Cited

U.S. PATENT DOCUMENTS

| | | | |
|---|---|---|---|
| 5,306,598 | 4/1994 | Kolosick | 430/264 |
| 5,415,980 | 5/1995 | Ohshima | 430/376 |

*Primary Examiner*—Thorl Chea
*Attorney, Agent, or Firm*—Breiner & Breiner

[57] ABSTRACT

It was found that good sensitizing activity in the red spectral region and without residual stain can be obtained with dyes of the general formula (I)

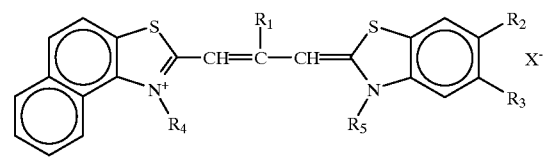

wherein $R_1$ is an alkyl group having 1 to 6 carbon atoms or a heterocyclic ring, $R_2$ and $R_3$ are hydrogen, methyl, or methoxy, but at least one of the groups $R_2$ and $R_3$ is not hydrogen, $R_4$ and $R_5$ are alkyl groups having 1 to 6 carbon atoms that can be substituted with hydroxyl groups, and $X^-$ is an anion.

The invention can be used for preparing silver images, for example, for reproduction in preprint operations for black and white or multicolor printing.

8 Claims, No Drawings

PHOTOGRAHIC SILVER HALIDE MATERIAL AND PROCESS FOR PREPARING SILVER IMAGES

BACKGROUND OF THE INVENTION

1. Field of the Invention

The invention involves a photographic silver halide material for preparing silver images, using a sensitizing dye that provides low stain at high sensitivity.

2. Description of the Related Art

The use of polymethine or cyanine dyes to spectrally sensitize silver halide emulsions has long been known. Numerous types of these dyes are described in relevant handbooks, for example, T. H. James "The Theory of the Photographic Process", $4^{th}$ edition, pages 194 ff, Mac Millan Publishing Co., New York, 1977. However, not all dyes of this class are equally suitable for use in silver halide emulsions.

Photographic silver halide materials, for example, for preparing black and white silver images for prepress operations, have a series of special requirements:

They must have the highest possible spectral sensitivity.
They must be rapidly processible.
The images should not show, as a result of rapid processing, troublesome stain from sensitizing dyes residues.

It has become customary in recent years to shorten the processing cycle for exposed silver halide films, which usually comprises treatment with at least three different aqueous baths for developing, fixing, and washing, by increasing the developer bath temperature and by using concentrated developer and fixing bath solutions. However, the sensitizing dyes are often not adequately removed from the layer during processing, and a troublesome residual stain remains. This can show, for example, in black and white images, as unsatisfactorily high minimum density relative to light of a certain wavelength, and in color images, as color adulteration.

It is indeed possible, within certain limits, to increase sensitization, that is, to increase spectral sensitivity, by increasing the quantity of sensitizer relative to the quantity of silver halide. However, the quantity of dye remaining in the image layer after processing also usually increases and consequently, so does stain.

It is known that the dye elimination capability of photographic materials during aqueous processing is enhanced by water-soluble groups on the dye molecule. Such groups are primarily acid groups, such as the sulfonic acid group or carboxyl group.

EP-A1-04 27 892 describes certain trinuclear merocyanine dyes as sensitizers for the red spectral range to enable good sensitivity with low stain. At least two of the substituents on these dye molecules are supposed to be special water-soluble groups in the form of a free acid, a salt, or in latent form. Examples of such groups are carboxylic and sulfonic acid groups and alkyl and aryl groups substituted with one of these acid groups.

International Patent Application WO 93/02389 describes a silver halide material for rapid processing to ultrahigh contrast and having low stain, based on a chloride-rich emulsion having a hydrazine compound and a contrast-enhancing amino compound. The sensitizer is a benzimidazole carbocyanine having at least one acid-substituted alkyl group on one of the imidazole nitrogen atoms.

U.S. Pat. No. 4,725,532 teaches that pepper is mitigated in high contrast materials having hydrazine compounds and a cationic cyanine, hemicyanine, or rhodacyanine dye, if the materials also contain ascorbic acid.

EP-A1-05 21 632 involves trimethine dyes based on benzothiazole, which are supposed to yield increased sensitivity in the red-sensitive layer of color films and a low tendency to color adulteration from diffusion into another layer.

There is further need for red sensitive materials having high sensitivity and minimal stain, particularly from the standpoint of making silver images by exposing silver halide films with red-emitting light sources, preferably lasers, and subsequent rapid processing.

SUMMARY OF THE INVENTION

Therefore, the problem involved in the invention is to make available a photographic material having high sensitivity in the red wavelength range and also yielding images with low stain in rapid processing. Another problem is to supply a process with which silver images can be prepared with very low stain.

These problems are solved by a photographic silver halide material comprising at least one photosensitive, silver halide emulsion layer on a support, the emulsion layer containing at least one sensitizing dye that sensitizes the silver halide for light in the 600 to 690 nm spectral range, characterized in that the sensitizing dye is of the general formula (I) and a process of exposing and processing the recording material.

DETAILED DESCRIPTION OF THE INVENTION

Specifically, it has been found surprisingly that photographic silver halide materials containing, in the silver halide emulsion layer, a sensitizing dye of the general formula (I)

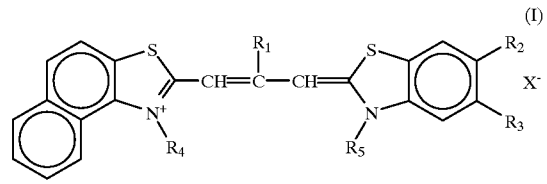

yield images having very low stain at high sensitivity to light of a wavelength between 600 and 690 nm.

In Formula (I), $R_1$ is an alkyl group of 1 to 6 carbon atoms or a heterocyclic ring, $R_2$ and $R_3$ are hydrogen, methyl, or methoxy, but at least one of the groups $R_2$ and $R_3$ is not hydrogen, $R_4$ and $R_5$ are alkyl groups of 1 to 6 carbon atoms, which can be substituted with a hydroxyl group, and $X^-$ is an anion.

This result is surprising to the expert, because the invention's dyes do not contain any of the known solubilizing groups in the molecule.

Examples of group $R_1$ are methyl, ethyl, propyl, butyl, isopropyl, isobutyl, t-butyl, straight chain or branched pentyl or hexyl, cyclopentyl, 1-, 2-, 3-, or 4-piperidyl, 2-, 3-, or 4-pyridyl, 2-, 3-, or 4-morpholyl, 1-, 2-, or 3-pyrrolidinyl, 2- or 3-tetrahydrothiophenyl, 2- or 3-thiophenyl, 2-, 3-, 4-, or 5-thiazolinyl, 1-, 3-, or 4-pyrazolyl, or 1-, 2-, or 4-imidazolyl.

Examples of $R_4$ and $R_5$ are methyl, ethyl, propyl, butyl, isopropyl, isobutyl, t-butyl, straight chain or branched pentyl or hexyl, hydroxymethyl, 1- or 2-hydroxyethyl, 2- or 3-hydroxypropyl.

The following sensitizing dyes are suitable examples for working the invention:

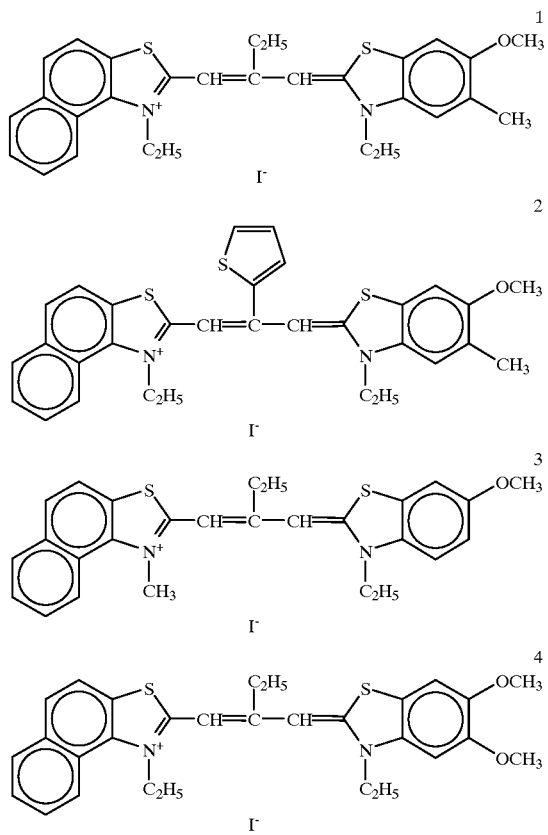

The quantity of sensitizing dye can be varied within wide limits. A preferred range is between $10^{-6}$ and $10^{-2}$ mole of dye per mole of silver halide.

The dye can be incorporated into the emulsion in a known manner, for example, as an aqueous solution, as a solution in nonaqueous solvents, such as alcohols or ketones, or as a finely divided solid suspension in an aqueous phase.

The emulsion of the photosensitive silver halide emulsion layer is preferably sensitized so that it is negative-working, that is, in the exposed areas, silver halide is reduced to silver on direct treatment of the imagewise exposed material with a negative developer, for example, one of the composition given in Example 1 below.

The recording material in a preferred embodiment of the invention contains a hydrazine compound. Such hydrazine compounds are known to increase contrast in the silver image. The hydrazine compound can be incorporated in a known manner in either one or more layers of the recording material. These can be layers that contain photosensitive silver halide as well as layers that are in a reactive relationship with the former, that is, these are arranged so that materials can diffuse from one into another layer, if a concentration gradient is maintained by reactions.

Examples of suitable hydrazine compounds are described in Research Disclosure 235 010 (November 1983), DE-27 25 743-A1, EP-00 32 456-B1, EP-01 26 000-A2, EP-01 38 200-A2, EP-02 03 521-A2, EP-02 17 310-A2, EP-02 53 665-A2, EP-03 24 391-A2, EP-03 24 426-A2, EP-03 26 443-A2, EP-03 56 898-A2, EP-04 73 342-A1, , EP-05 01 546-A1, EP-04 81 565-A1, EP-05 98 315-A1, and EP-04 44 506-A.

Preferred hydrazine compounds are described by the general formula (H)

B-phenyl-NHNH-L-G                      (H)

B is a ballast group, G is an activating group, and L is one of the groups —CO— and —CO—CO—. "Phenyl" means a benzene ring to which B and the hydrazine group are linked, preferably in the para position.

Preferred ballast groups are not electron-attracting, for example, straight chain or branched alkyl groups (for example, methyl, ethyl, n-propyl, isopropyl, n-butyl, isobutyl, n-hexyl, n-octyl, t-octyl, n-decyl, n-dodecyl, and similar groups), alkoxy groups containing one of the above-named alkyl groups as the alkyl, acylamino groups, such as acetylamino, propanoylamino, butanoylamino, octanoylamino, benzoylamino, alkyl and aryl sulfamido, guanidyl, and similar groups.

The groups cited can themselves be substituted with the usual photographic ballast groups, known for incorporated diffusion-resistant couplers and other immobilized photographic additives. Such ballast groups contain typically at least eight carbon atoms and can be selected from relatively inert aliphatic or aromatic groups, for example, alkyl, alkoxy, phenyl, alkylphenyl, phenoxy, alkylphenoxy, arylacyl, arylamido, alkyl-pyridinium-1-ylamido, and similar groups.

The alkyl and alkoxy groups, including any ballast groups, contain preferably 1 to 20 carbon atoms, the acylamino groups preferably 2 to 21 carbon atoms. However, these groups can contain up to 30 or more carbon atoms. Particularly preferred are methoxyphenyl, tolyl, ballasted butyramidophenyl, butyl sulfonamido, and toluyl sulfonamido.

Preferred hydrazine compounds are those whose ballast groups also contain an adsorption-enhancing group. Such groups promote adsorption of the molecule on the surface of the silver halide crystals, and are known as such. Typically, they contain at least a sulfur or nitrogen atom that can form a silver complex or otherwise has an affinity for the silver halide surface. Preferred examples are thiourea, thiouronium, heterocyclic thioamide, and triazole groups.

G is preferably hydrogen, optionally substituted alkyl (for example, methyl, hydroxymethyl, monofluoromethyl, pyridinomethyl, phenoxymethyl, and alkoxymethyl, such as methoxymethyl), optionally substituted aralkyl (for example, benzyl, o-hydroxybenzyl), and optionally substituted aryl (for example, phenyl, 3,5-dichlorophenyl, o-methanesulfonamidophenyl, 4-methanesulfonylmethyl, and 2-hydroxymethylphenyl). Alkyl groups having electron-attracting substituents, for example, cationic groups having a quaternary nitrogen atom, such as pyridinium and imidazolium, are particularly preferred.

G can also be further substituted, for example, with alkyl, aralkyl, alkenyl, alkinyl, alkoxy, aryl, substituted amino, ureido, urethane, aryloxy, sulfamoyl, carbamoyl, alkyl or aryl thio, alkyl or aryl sulfonyl, alkyl or aryl sulfinyl, hydroxy, halogen, cyan, sulfo, aryloxycarbonyl, acyl, alkoxycarbonyl, acyloxy, carbamide, sulfonamide, carboxyl, phosphamide, diacylamino, and imide groups.

G can also be selected so that the L-G portion of the molecule is separated by ring formation, as described in EP-B-02 53 665.

Examples of suitable hydrazine compounds are

H-1
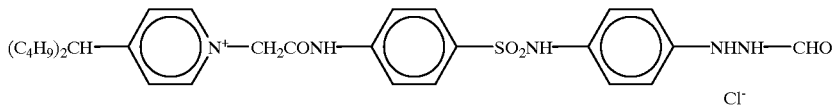

H-2
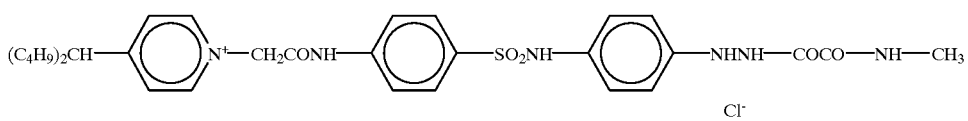

H-3
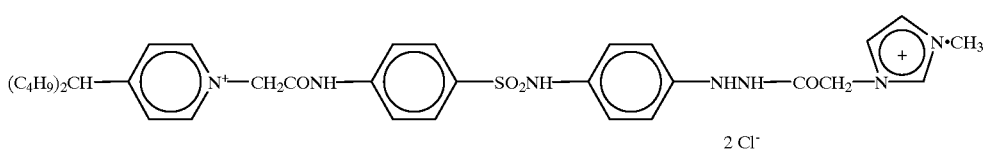

H-4
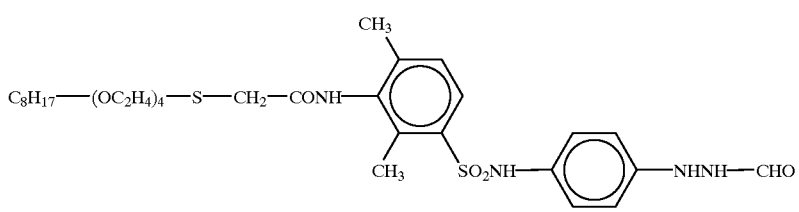

H-5
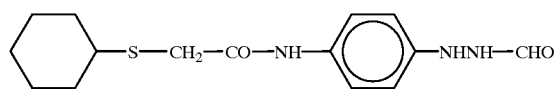

H-6
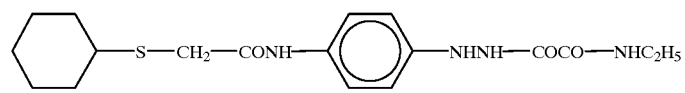

H-7
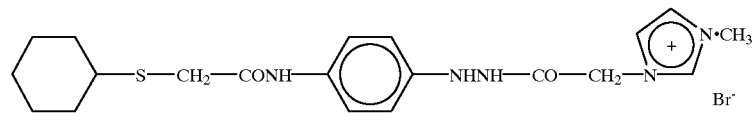

H-8
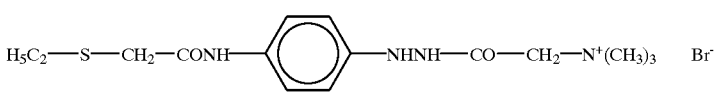

H-9
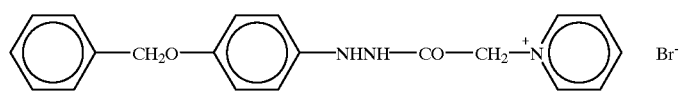

H-10
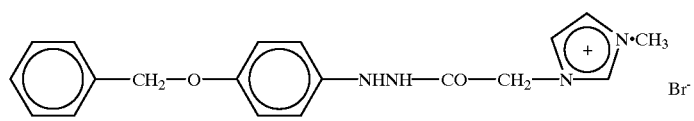

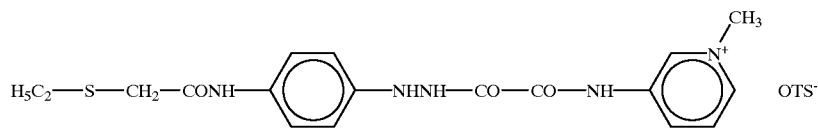
H-11
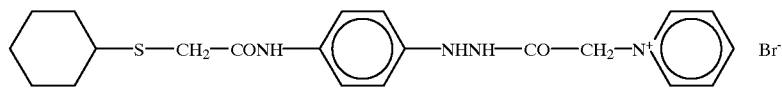
H-12
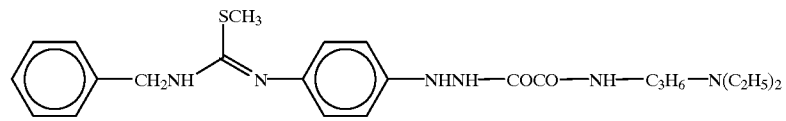
H-13
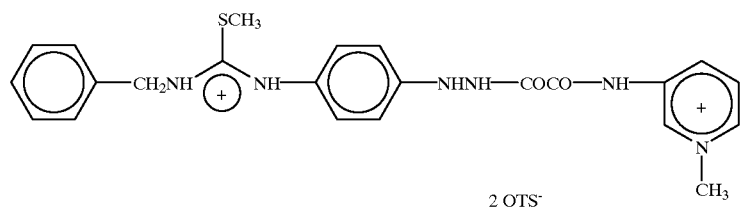
H-14
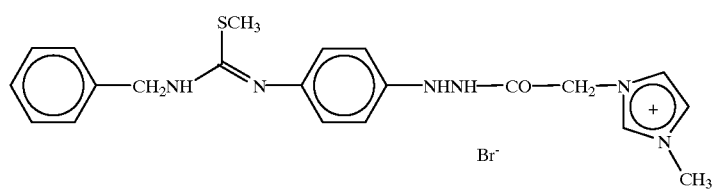
H-15
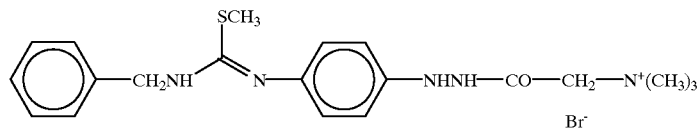
H-16
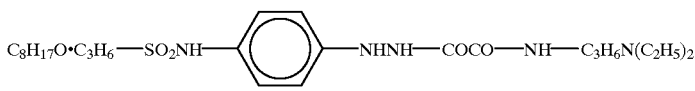
H-17
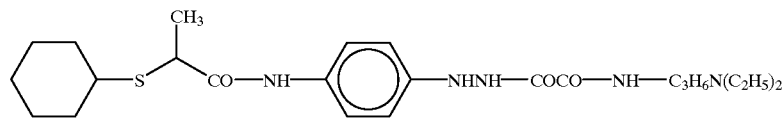
H-18
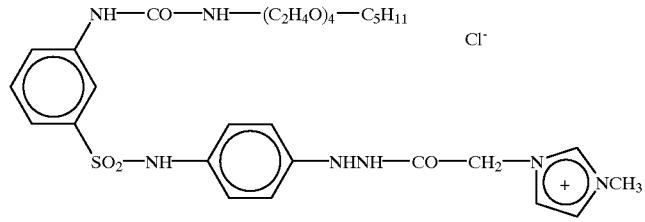
H-19

H-20

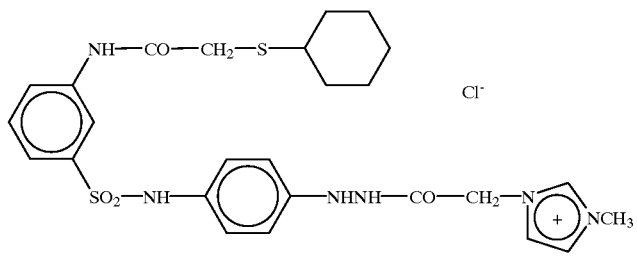

H-21

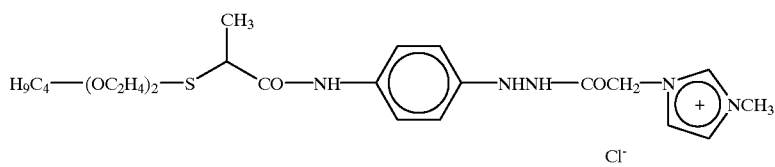

The quantity of hydrazine compound is preferably between $10^{-6}$ and $10^{-2}$ mole per mole of silver halide.

Recording materials containing a contrast-enhancing amino compound are also preferred. Such an amino compound can be present either alone or in addition to the contrast-enhancing hydrazine compound.

Examples of suitable contrast-enhancing amine compounds are disclosed in U.S. Pat. No. 4,914,003, EP-A-06 18 491, and EP-A-06 63 611.

Preferred amino compounds contain at least one secondary or tertiary amino group and in addition, a group having a quaternary nitrogen atom, a polyoxyalkylene chain, a thioether or thioketone group, a nitrile group, a sulfonyl urea or urethane group, or a guanidine group.

Examples of suitable amino compounds are

A-1

A-2

A-3
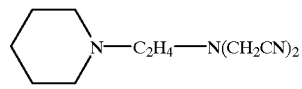

A-4
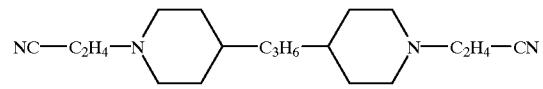

A-5
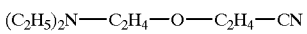

A-6
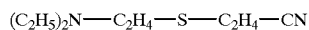

A-7
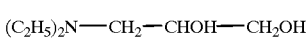

A-8
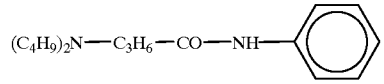

A-9
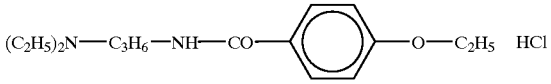

A-10

A-11
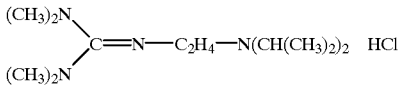

A-12
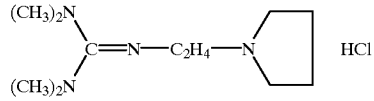

A-13
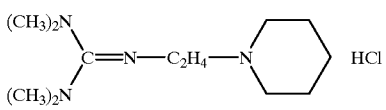

A-14
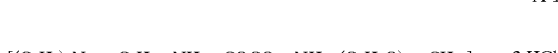

A-15
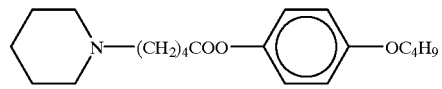

A-16
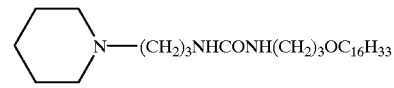

-continued
A-17
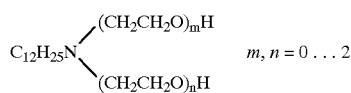
A-18
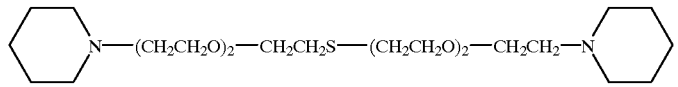
A-19
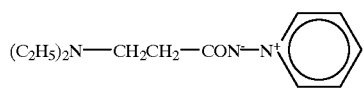
A-20
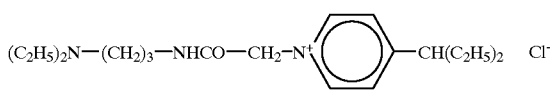
A-21
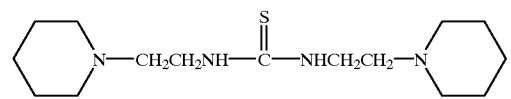
A-22
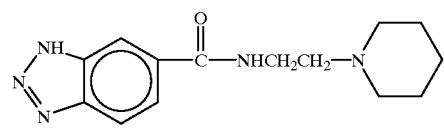
A-23
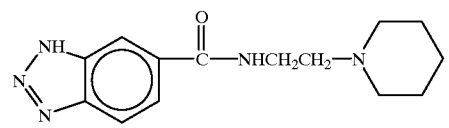
A-24
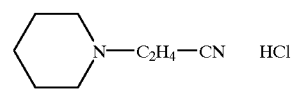
A-25
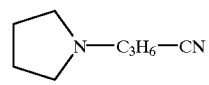
A-26
A-27
A-28
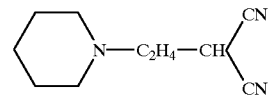
A-29
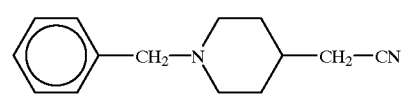
A-30
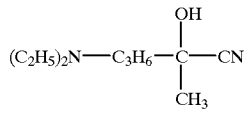
A-31
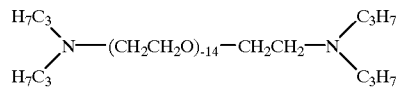
A-32
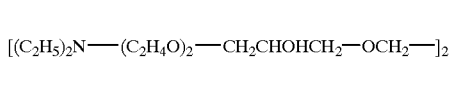
A-33
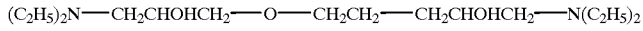
A-34
A-35
A-36
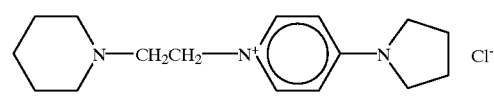
A-37
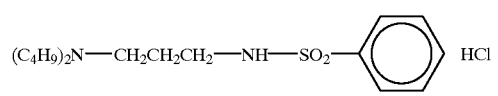

-continued

A-38

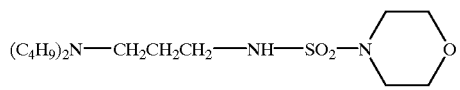

A-39

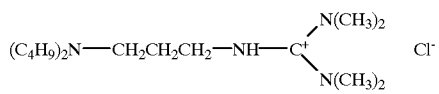

A-40

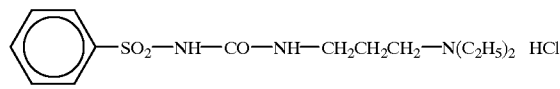

A-41

[(C$_4$H$_9$)$_2$N—CH$_2$CH$_2$CH$_2$—N—CH$_2$—CH$_2$—CH—OCH$_2$—]$_2$
  |   |
  COCH$_3$   OCOCH$_3$

A-42

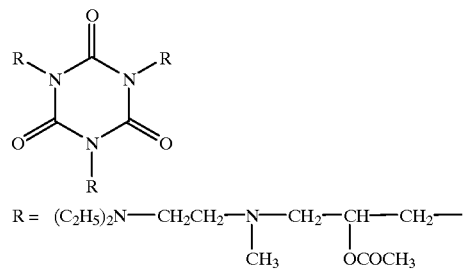

R = (C$_2$H$_5$)$_2$N—CH$_2$CH$_2$—N—CH$_2$—CH—CH$_2$—
  |   |
  CH$_3$   OCOCH$_3$

The photosensitive silver halides of the invention's recording materials are silver chloride, silver bromide, silver chlorobromide, silver bromoiodide, or silver chlorobromoiodide. Bromide and bromoiodide are preferred. These can be monodisperse or polydisperse, and can have a uniform composition, but can also be grains having a core-shell structure as well as mixtures of grains of different compositions and grain size distribution. These are prepared with the use of a hydrophilic colloidal binder, preferably gelatin. The silver halide grains can be spherical, polyhedral, or tabular. Methods for preparing suitable photosensitive silver halide emulsions are known to the expert and are summarized, for example, in Research Disclosure 365 044, Section I to IV (September 1994).

Preferred silver halide emulsions for the invention's recording materials are prepared by controlled twin jet precipitation and have cubic grains. Advantageous emulsions have at least 80 percent by weight of the silver halide in cubic form. Particularly preferred are monodisperse emulsions, that is, those having a variation coefficient (quotient of standard deviation and average value) in grain size of less than 0.30. Grain size is understood as the edge length of a cube having the same volume as the actual grain.

The grain volume of the silver halide grains in the emulsions depends on the required sensitivity and can correspond, for example, to cubic grains having 0.1 to 0.7 μm edge length. The preferred range is between 0.15 and 0.30 μm. Noble metal salts, particularly salts of rhodium or iridium, can be present in the usual quantities to regulate photographic properties during emulsion preparation.

The emulsions are preferably chemically sensitized. Suitable processes are sulfur, reduction, and noble metal sensitization, which can also be combined. Gold or iridium compounds are used, for example, in the latter. Sensitization is conducted preferably in the presence of salts of organic thiosulfonic acids, such as p-toluene thiosulfonic acid.

The emulsions can contain conventional antifoggants. Preferred are optionally substituted benzotriazole, 5-nitroindazole, and 1-phenyl-5-mercaptotetrazole. These agents can be added at any time during emulsion preparation, or can be contained in an auxiliary layer of the photographic material. Photographic properties can be improved can be improved by adding to the emulsion, before or after chemical ripening, an iodide, preferably an alkali iodide, in a quantity of about 0.5 to 10 millimoles per mole of silver.

The emulsions can also contain known polymer dispersions which, for example, improve the dimensional stability of the photographic material. These are, as a rule, latexes of hydrophilic polymers in an aqueous matrix. Examples of suitable polymer dispersions are cited in Research Disclosure 176 043, Section IX B (December 1978). Preferred are polymers and copolymers of esters of acrylic acid and methacrylic acid, C$_1$ to C$_6$ esters, for example, polyethylacrylate being preferred. The preferred particle size of these polymer latexes is between 20 and 100 nm.

The photosensitive layers of the photographic materials can be hardened by the addition of a hardening agent. Examples of hardening agents are cited in Research Disclosure 365 044, Section II B (September 1994). The hardening agent can be added to the emulsion or can be applied through an auxiliary layer, for example, an outer protective layer. Examples of suitable hardening agents are aldehydes, such as formaldehyde or glutaraldehyde, vinyl sulfones, s-triazines, aziridines, carbodiimides, carbamoyl pyridinium compounds, and monofunctional and bifunctional carbamoyl imidazolium compounds. A preferred hardening agent is hydroxychlorotriazine.

The photographic material can contain other additives that are conventional and known to yield specific properties. Examples of such agents are described in Research Disclosure 365 044 (September 1994), in Sections VI (Brighteners), IX A (Coating Aids), IX B (Plasticizers and Slip Agents), and IX D (Matte Agents). If specified for making color images, the material can also contain color couplers and other additives described in Sections XII and XIII.

The emulsions generally contain between 30 and 150 g of gelatin per mole of silver. The range between 40 and 100 g per mole of silver is preferred.

The invention also includes a process for making silver images characterized in that an above-described photographic material is exposed imagewise and processed by development in an aqueous developer solution, fixed in the usual manner, washed, and dried.

The process is conducted preferably as rapid processing having a development time of 30 seconds at most and a correspondingly adapted development temperature.

The developer solutions used in the invention contain preferably a dihydroxybenzene developer, for example, hydroquinone, pyrocatechol, methyl hydroquinone, or chlorohydro-quinone and an antioxidant, preferably an alkali sulfite in a concentration above 0.3 mole per liter. Particularly preferred solutions have a pH of 9–11. Such developer solutions are also stable in use and yield images that are largely fog-free. Similarly useful are developer solutions having a developer of the ascorbic acid type, for example, L-ascorbic acid, D-ascorbic acid, L-erythroascorbic acid, 6-desoxy-L-ascorbic acid, imino-L-erythroascorbic acid, or sugar derivatives of these acids. Also suitable are developer solutions containing developers of the dihydroxybenzene type as well as the ascorbic acid type.

Preferred developer solutions contain known superadditive developer aids, for example, N-methyl-p-aminophenol or 1-phenyl-pyrazolidinone-3, or derivatives of these compounds.

Similarly preferred are developers containing stabilizers from the benzotriazole and mercaptotetrazole groups. Examples of such stabilizers are 1-phenyl-5-mercaptotetrazole, 1-(4-hydroxy-phenyl)-5-mercaptotetrazole, 1-(1-naphthyl)-5-mercaptotetrazole, 1-cyclohexyl-5-mercaptotetrazole, 1-(4-chlorophenyl)-5-mercapto-tetrazole, 1-(3-capramidophenyl)-5-mercaptotetrazole, benzo-triazole, 5-chlorobenzotriazole, 5-bromobenzotriazole, 5-methylbenzotriazole, 5-nitrobenzotriazole, 5-benzoylaminobenzotriazole, 1-hydroxymethylbenzotriazole, and 6-cyanobenzotriazole.

The invention can be used to prepare silver images, preferably from black and white negative images having ultrahigh contrast, particularly for reproduction in preprinting operations for black and white and multicolor printing.

The quantities of emulsion components in the following examples are relative to 1 mole of silver, unless otherwise stated. The comparison compounds are the known dyes V-1 to V-8:

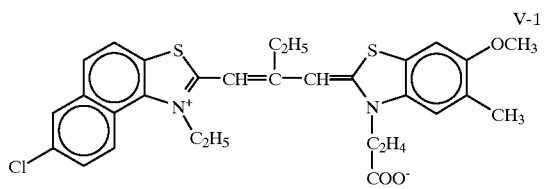
V-1

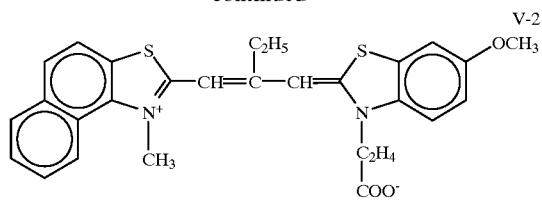
V-2

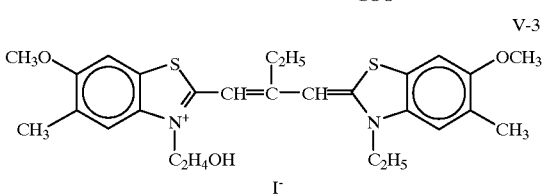
V-3

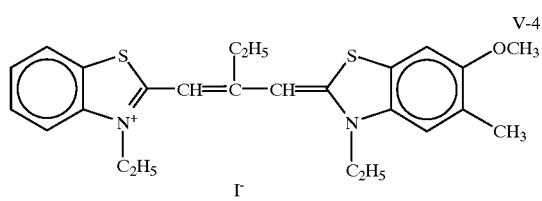
V-4

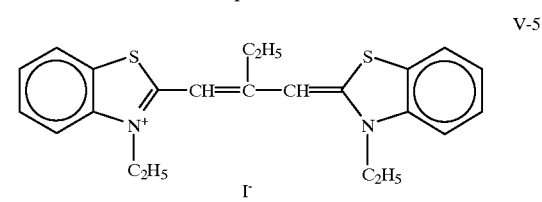
V-5

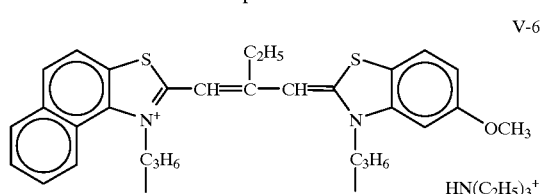
V-6

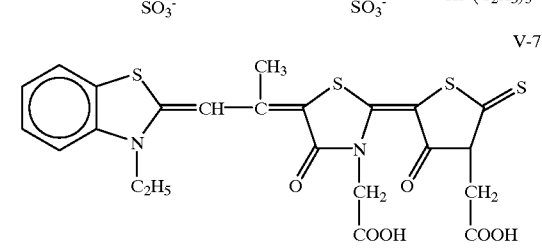
V-7

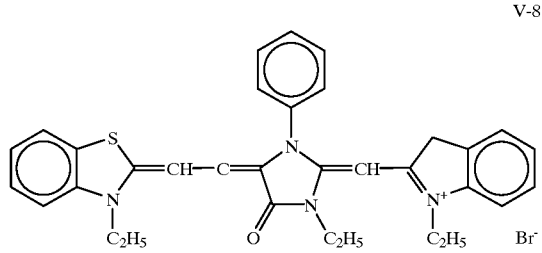
V-8

EXAMPLE 1

A silver bromoiodide emulsion having cubic grains of 0.25 μm edge length and 2 mole percent iodide was prepared by pAg-controlled twin jet precipitation in a gelatin solution. Soluble salts were removed from the emulsion by flocculation, and the coagulate was redispersed with additional gelatin. The resulting emulsion was ripened chemically by the addition of 0.2 millimole of thiosulfate and 0.03 millimole of tetrachloroauric acid. To portions of this emulsion were added 5 millimoles of potassium iodide, the sensitizing dye listed in Table 1, 300 mg of 7-hydroxy-1-methyl-1,3,4-triazaindolizine, 100 mg of 5-nitroindazole, 4 g of hydroquinone, 15 g of polyethylacrylate as an aqueous latex, and a surfactant. The resulting emulsions, ready for coating, were applied together with a protective layer overcoating onto a polyethylene terephthalate support. The protective layer contained, per square meter, 1 g of gelatin, 0.3 millimole of formaldehyde, 0.5 g of colloidal silica, a polyethylene dispersion, and a matte agent. The resulting recording material contained 4.5 g of silver per square meter.

Samples of these materials were exposed with a flash lamp ($2 \times 10^{-3}$ sec) through a red filter and a density gradation wedge. The exposed samples were processed in a roll developing machine for 30 seconds at 35° C. with a developer of the composition given below, treated in a commercial fixing bath, washed for 30 seconds, and dried. The sensitivity S of the processed samples was measured as the reciprocal of the exposure required for the density 1.0, relative to the value 100 for Sample 1. Stain was judged visually. The results are listed in Table 1.

| Developer Composition (all components in g) | |
| --- | --- |
| Water | 500 |
| Sodium bisulfite | 50 |
| Potassium hydroxide | 27 |
| Ethylenediamine tetraacetic acid, trisodium salt | 3.7 |
| Hydroquinone | 25 |
| Potassium bromide | 4 |
| Benzotriazole | 0.3 |
| Phenylmercaptotetrazole | 0.05 |
| 4-hydroxymethyl-4-methyl-1-phenylpyrazolidinone | 1 |
| Boric acid | 3 |
| Sodium hydroxide | 24 |
| Diethylene glycol | 40 |
| Water to make 1 liter, pH adjusted to 10.5, at 22° C. | |

TABLE 1

| | Sensitizer | | | |
| --- | --- | --- | --- | --- |
| Sample No. | No. | Weight (mg) | S | Stain |
| 1 | V8 | 70 | 100 | blue |
| 2 | V7 | 150 | 400 | weak reddish |
| 3 | V6 | 70 | 160 | red-violet |
| 4 | V5 | 80 | 350 | red |
| 5 | V4 | 80 | 500 | weak red |
| 6 | V3 | 80 | 500 | weak red |
| 7 | V2 | 80 | 1000 | deep red |
| 8 | V2 | 40 | 500 | deep red |
| 9 | V1 | 80 | 500 | red |
| 10 | 1 | 40 | 1100 | none |
| 11 | 1 | 80 | 1500 | none |
| 12 | 1 | 130 | 1700 | light red |
| 13 | 2 | 40 | 500 | none |
| 14 | 3 | 40 | 700 | none |
| 15 | 3 | 80 | 1200 | light reddish |
| 16 | 3 | 130 | 1300 | light red |

EXAMPLE 2

A silver bromoiodide emulsion having cubic grains of 0.17 μm edge length and 2 mole percent iodide was prepared by pAg-controlled twin jet precipitation in a gelatin solution. The emulsion was flocculated as in Example 1, washed, redispersed, and ripened chemically with 0.01 millimole of hexachloroplatinic acid, 0.4 millimole of thiosulfate, and 0.1 millimole of tetrachloroauric acid. Then, 5 millimoles of potassium iodide, 300 mg of 7-hydroxy-1-methyl-1,3,4-triazaindolizine, 200 mg of 5-nitroindazole, 0.15 millimole of 1-pyridiniumacetyl-2-(4-benzyl-oxyphenyl)hydrazine bromide (Compound H-9), 0.6 g of N-(3-di-butylaminopropyl)benzenesulfonamide hydrochloride (Compound A-37), 1.25 g of polyethylene oxide (mole mass 4000), and the sensitizing dyes listed in Table 2 were added in each case to samples of the emulsion.

The resulting ready-to-coat emulsions were applied together with a coating solution of a protective layer having 0.9 g/m² of gelatin on a polyethylene terephthalate support backed with an antistatic and anticurl coating. The silver coating weight was 3.5 g per square meter.

Samples of the resulting materials were exposed as described in Example 1 and processed to silver images. In addition to sensitivity and stain, minimum and maximum density, Dmin and Dmax, and average gradation G between densities 0.4 and 3.5 were determined.

The results listed in Table 2 show that the invention's dyes do not cause stain in high contrast films on processing and do not impair other photographic properties.

TABLE 2

| | Sensitizer | | | | | | |
| --- | --- | --- | --- | --- | --- | --- | --- |
| Sample | No. | Amount (g) | Dmin | Dmax | S | G | Stain |
| 1 | V7 | 170 | 0.053 | 6.2 | 100 | 20 | weak pink |
| 2 | V6 | 100 | 0.056 | 5.5 | 45 | 15 | weak blue |
| 3 | V6 | 50 | 0.075 | 5.9 | 76 | 18 | deep blue |
| 4 | 1 | 100 | 0.052 | 6.1 | 120 | 16 | none |
| 5 | 1 | 50 | 0.048 | 6.0 | 61 | 17 | none |

EXAMPLE 3

Samples of some materials from Example 2 were exposed on a phototypesetting exposure unit having a helium-neon laser (Linotronic 300, Hell Company), with halftone screens of 60 lines per cm and with fonts. The samples were processed as in Example 2, but with 25 seconds development. Sensitivity was determined at the laser energy setting for a 50% dot. Dot quality and stain were judged visually. Results are shown in Table 3.

TABLE 3

| Sample | Sensitivity | Dot Quality | Stain |
| --- | --- | --- | --- |
| 1 | 100 | very good | weak pink |
| 3 | 55 | very good | blue |
| 4 | 200 | very good | none |
| 6 | 50 | adequate | weak pink |

Sample 6 used for comparison does not contain a hydrazine and is otherwise the same as Sample 1.

What is claimed is:

1. A photographic silver halide material comprising at least one photosensitive, silver halide emulsion layer on a support, the emulsion layer containing at least one sensitizing dye that sensitizes the silver halide for light in 600 to 690 nm spectral range, said sensitizing dye having the formula (I)

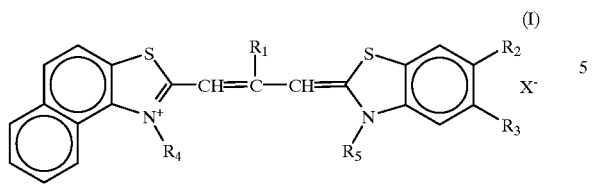

wherein $R_1$ is an alkyl group having 1 to 6 carbon atoms or a heterocyclic ring, $R_2$ and $R_3$ are hydrogen, methyl, or methoxy, but at least one of the groups $R_2$ and $R_3$ is not hydrogen, $R_4$ and $R_5$ are alkyl groups having 1 to 6 carbon atoms that can be substituted with hydroxyl groups and $X^-$ is an anion; wherein said sensitizing dye does not contain a sulfonic acid group or a carboxyl group in its molecule.

2. The material according to claim 1, wherein the silver halide emulsion layer is a negative-working layer.

3. The material according to claim 1 or 2, including a hydrazine compound in the silver halide emulsion layer or in a layer reactively related thereto.

4. The material according to one of claims 1 to 3, including a contrast-enhancing amino compound in the silver halide emulsion layer or in a layer reactively related thereto.

5. The material according to one of claims 1 to 4, wherein the sensitizing dye is:

1

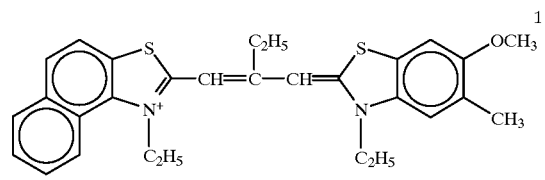

or

2

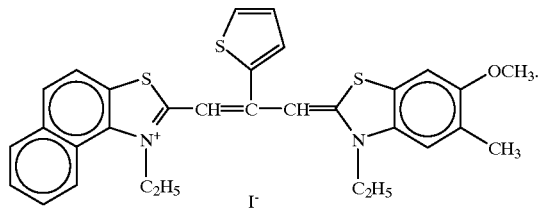

6. The material according to one of claims 1 to 4, wherein the silver halide emulsion is a silver bromide or a silver bromoiodide emulsion.

7. A process for preparing a silver image, comprising exposing and processing the photographic recording material of one of the preceding claims.

8. The process according to claim 7, wherein the processing time is 30 seconds or less.

* * * * *

UNITED STATES PATENT AND TRADEMARK OFFICE
CERTIFICATE OF CORRECTION

PATENT NO. : 6,150,083
DATED : November 21, 2000
INVENTOR(S) : Francois Varescon et al.

Page 1 of 1

It is certified that error appears in the above-identified patent and that said Letters Patent is hereby corrected as shown below:

Column 12,
Example A-35 should read

Column 20, claim 5,
After structural formula 2, insert

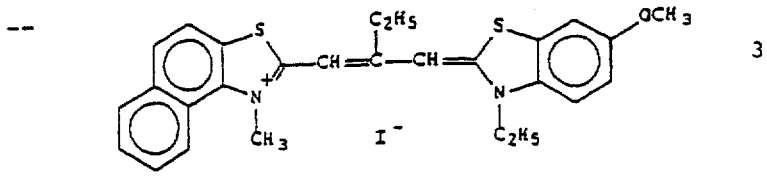

3

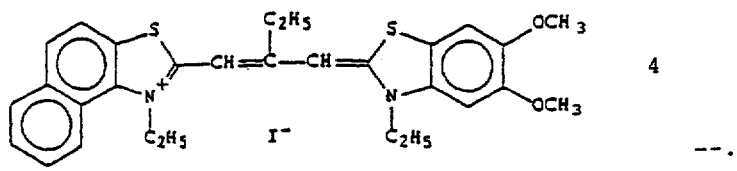

4

--.

Signed and Sealed this

Fourth Day of December, 2001

Attest:

*Nicholas P. Godici*

NICHOLAS P. GODICI
*Attesting Officer*    *Acting Director of the United States Patent and Trademark Office*